(12) United States Patent
Ohuchi et al.

(10) Patent No.: US 7,468,421 B2
(45) Date of Patent: *Dec. 23, 2008

(54) DEPILATORIES AND AGENTS FOR EXTERNAL USE

(75) Inventors: Atsushi Ohuchi, Tochigi (JP); Akemi Kobayashi, Tochigi (JP); Akira Hachiya, Tochigi (JP)

(73) Assignee: Kao Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/026,090

(22) Filed: Jan. 3, 2005

(65) Prior Publication Data

US 2005/0112079 A1 May 26, 2005

Related U.S. Application Data

(63) Continuation of application No. 10/110,226, filed as application No. PCT/JP00/07218 on Oct. 18, 2000, now Pat. No. 6,884,772.

(30) Foreign Application Priority Data

Oct. 21, 1999 (JP) ............................... 11-299305

(51) Int. Cl.
*C07K 7/00* (2006.01)
(52) U.S. Cl. ............................. 530/326; 514/2; 514/19; 424/70.1
(58) Field of Classification Search ................. 530/326; 514/2, 19; 424/70.1
See application file for complete search history.

(56) References Cited

U.S. PATENT DOCUMENTS

| | | | | |
|---|---|---|---|---|
| 2,823,168 A | * | 2/1958 | Stonehill | ........................ 8/161 |
| 3,527,559 A | * | 9/1970 | Sliwinski | ........................ 8/161 |
| 4,139,619 A | | 2/1979 | Chidsey, III | |
| 5,306,808 A | | 4/1994 | Wakimasu et al. | |
| 5,468,476 A | * | 11/1995 | Ahluwalia et al. | ............ 424/73 |
| 5,519,058 A | | 5/1996 | Gonick et al. | |
| 6,093,748 A | | 7/2000 | Ahluwalia et al. | |
| 6,203,784 B1 | * | 3/2001 | Martin et al. | ................. 424/73 |
| 6,358,536 B1 | * | 3/2002 | Thomas | ...................... 424/608 |
| 6,375,948 B1 | | 4/2002 | Tsuji et al. | |
| 6,410,007 B1 | * | 6/2002 | Banting et al. | ........... 424/78.35 |
| 6,465,421 B1 | * | 10/2002 | Duranton et al. | ................ 514/1 |
| 2001/0056068 A1 | | 12/2001 | Chwalisz et al. | |

FOREIGN PATENT DOCUMENTS

| | | |
|---|---|---|
| EP | 0 129 197 A2 | 12/1984 |
| EP | 0 748 636 | 12/1996 |
| WO | WO 99/38472 | 8/1999 |

OTHER PUBLICATIONS

Merkel L. A. (Biochemical and Biophysical Research Communications 192(3):1319-1326, 1993).*
English Abstract of EP 2769225, issued Apr. 1999.*
English Abstract of Japanese patent 04-099708, issued Mar. 1992.*
Banting, J.D. (Journal of Hypertension 14(8):975-981, 1996).*
Partial English Translation of Takashi Kakihara, "Practical Knowledge for Cosmetics", Toyokeizai Sinnpo 1981, p. 109.*
English abstract of JP 7-002677, issued Jan. 1995.*
English abstract of JP 7-206843, issued Aug. 1995.*
Merck Research Laboratories Division of Merk & Co., Inc., "The Merck Index", Twelfth edition, No. 3616, p. 605, 1996.
S. Kurbel, et al., Medical Hypotheses, vol. 53, No. 5, pp. 402-406, XP-009009966, "Minoxidil and Male-Pattern Alopecia: A Potential Role for a Local Regulator of Sebum Secretion With Vasoconstrictive Effects?", Nov. 1999.
Derwent Abstracts, AN 2000-515332, XP-002239520, CN 1 255 329, Jun. 7, 2000.
Patent Abstracts of Japan, JP 04-099708, Mar. 31, 1992.

* cited by examiner

*Primary Examiner*—David Lukton
(74) *Attorney, Agent, or Firm*—Oblon, Spivak, McClelland, Maier & Neustadt, P.C.

(57) ABSTRACT

This invention relates to depilatories and external preparations, each of which contains endothelin or its agonist, and also to a depilating method characterized by administering endothelin or its agonist.

As the depilatories and external preparations according to the present invention inhibit growth of hair in mammalian skin, their application to the human body as drugs or cosmetics permits safe and effective removal of hair from the body. These depilatories and external preparations are also usable as wool harvesting preparations.

8 Claims, 2 Drawing Sheets

DEPILATORIES AND AGENTS FOR EXTERNAL USE

The present application is a continuation of U.S. application Ser. No. 10/110,226, filed on Aug. 15, 2002, which is a National Stage (371) of International Application PCT/JP00/07218, filed on Oct. 18, 2000 now U.S. Pat. No. 6,884,772, which claims priority to JP 11-299305, filed on Oct. 21, 1999.

TECHNICAL FIELD

This invention relates to depilatories and external preparations, which are useful as drugs, cosmetics and animal drugs.

BACKGROUND ART

Mammalian hair on the scalp and body biologically provides protection for important organs such as the head, the chest or the brisket, and the arm and legs. In recent years, however, hair on the human arms and legs is not considered to be preferred from the standpoint of makeup, beauty and external attraction, resulting in a tendency to remove hair from the body.

Conventionally known removal methods of hair from the body include, in addition to mechanical removal methods making use of a shaver, tweezers or the like, depilating methods which chemically decompose hair fibers or prevent, inhibit or retard hair growth. Such removal methods of body hair, however, tend to give physical or chemical irritations to the skin. Even from the standpoint of hair growth inhibition, they are not considered to be sufficient yet so that upon an elapsed time of a certain period, body hair must be removed again. There is, accordingly, an outstanding desire for a reduction to the irksomeness of removal of hair from the body.

In animals, on the other hand, paying attention to the existence of hair removing activity on epidermal growth factor (EGF), attempts to use EGF as wool harvesting preparations are finding practical utility. This application has merits in that sheep are free of potential cut damages and wool is improved in both yield and quality, for example, wool so harvested is uniform in length and is round at free ends. Development of a safe and economical depilatory is also meaningful in such a field.

An object of the present invention is to provide a depilatory and external preparation, each of which inhibits growth of hair in mammalian skin and is useful as a drug, cosmetic or animal drug.

DISCLOSURE OF THE INVENTION

The present inventors have proceeded with an investigation for substances having depilatory effects. As a result, it has been found that endothelin and its agonists have excellent effects for the inhibition of hair growth.

Described specifically, the present invention provides a depilatory and external preparation, each of which comprises endothelin or an agonist therefor.

The present invention also provides a depilating method characterized by administering endothelin or an agonist therefor.

BEST MODES FOR CARRYING OUT THE INVENTION

Figure 1:
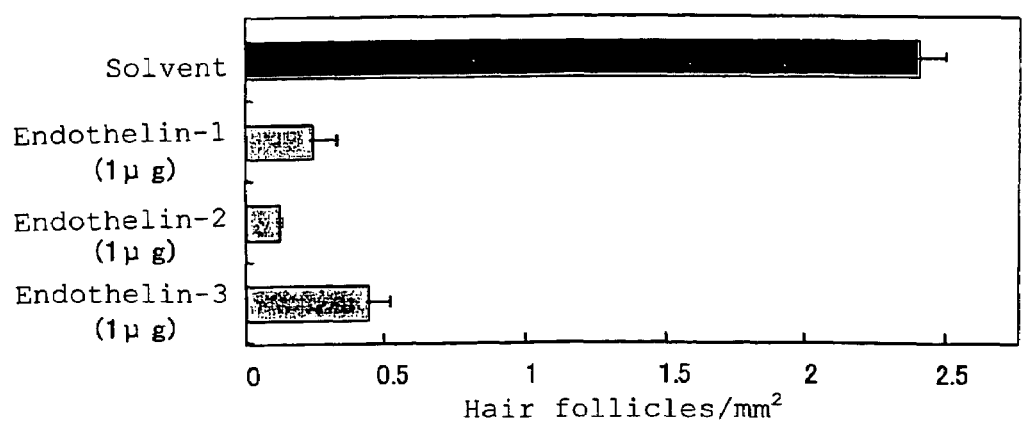
FIG. 1 diagrammatically illustrates effects of endothelin isoforms for decreasing the number of growth-phase hair follicles.

Endothelin is a physiologically active substance, which directly or indirectly causes persistent contraction of vascular and non-vascular smooth muscles. In recent years, the role of endothelin in ontogenesis has been clarified, and elucidation of the roles of endothelin in various cells such as gliacytes, renal mesangial cells and melanocytes is also underway. However, absolutely no report has been made as to how endothelin acts on the growth of hair. Further, use of endothelin as an external preparation is not known.

Endothelin is a peptide composed of 21 amino acid residues, and to date, it is known to include three isoforms, endothelin-1, endothelin-2 and endothelin-3. In the depilatory and external preparation according to the present invention, all the isoforms are usable, although use of endothelin-1 is preferred. The above-mentioned individual isoforms of endothelin are activated from their corresponding preproteins, in other words, big endothelins under the action of an in vivo enzyme (endothelin-converting enzyme), and such preproteins are also usable in the depilatory according to the present invention.

Further, endothelin agonists and their peptide fragment sequences having agonistic effects are also useful in the depilatory according to the present invention. Illustrative of the endothelin agonists are Sarafotoxin-6C and [Ala$^{1, 3, 11, 15}$]-endothelin-1 [Biochem. Biophys. Res. Commun., 182, 144 (1992)], whereas illustrative of the peptide fragment sequences having agonistic effects are endothelin-1 fragment 11-21 [FEBS Lett., 311; 12 (1992)], IRL1620 (N-succinyl-[Glu$^9$, Ala$^{11, 15}$]ET-1(8-21)) and BQ3020 (N-acetyl-[Ala$^{11,15}$]ET-1(6-21)).

Such endothelin can be separated and purified from a culture supernatant of endothelin-producing cells or a disrupted solution thereof, can be synthesized by peptide chemistry, or can be produced by a genetic engineering technique while making use of DNA having a base sequence encoding endothelin.

The depilatory effects of endothelin in the present invention are based on effects that inhibit hair growth by causing transition of growth-phase hair follicles into regressing phase (catagen) as will be described subsequently in Example 3. Therefore, the depilatory and external preparation according to the present invention can be used for human and all kinds of cattle, and no limitation is imposed on the kind or site of hair to which they are applied.

The administration route of the depilatory according to the present invention can be chosen, from transdermal administration, topical intracutaneous administration, systemic administration or the like, depending upon the purpose of administration and/or the kind and/or site of hair to which the depilatory is applied.

When the external preparation or depilatory according to the present invention is used as a transdermal preparation, the content of endothelin can be set preferably at 0.01 to 10 wt. % in general, with a range of from 0.1 to 1 wt. % being particularly preferred, from the viewpoint of depilatory effects, economy and the like.

When the depilatory according to the present invention is used as a topical intracutaneous preparation, on the other hand, the content of endothelin can be set preferably at 0.1 to 100 μg/administration in general, with a range of from 1 to 10 μg/administration being particularly preferred. Further, when used as a preparation for systemic administration, endothelin can be administered preferably at 0.01 to 100 mg/kg-body weight in general, with a range of from 0.1 to 10 mg/kg-body weight being particularly preferred.

When employed as an animal drug, subcutaneous or intraperitoneal administration is effective for systemic administration, and intracutaneous administration is effective for topical administration. Continuous transdermal administration is also effective. In this case, however, it is more effective to administer it in a form sealed in liposome to enhance transdermal absorption [R. M. Hoffman, J. Drug Target, 5, 67 (1998)].

To the depilatory and external preparation according to the present invention, one or more ingredients having hair growth inhibitory and/or depilatory effects, such as keratolytic agents and thioglycolic acid and salts thereof, may be added as desired, in addition to endothelin. Examples of the keratolytic agents can include lactic acid, bioprase, salicylic acid, glycolic acid, citric acid, and malic acid. Examples of the salts of thioglycolic acid, on the other hand, can include, in addition to its sodium, potassium and ammonium salts, its alkanolamines such as its monoethanol amines, diethanol amines and triethanol amines. The preferred content of the keratolytic agent or thioglycolic acid or the salt thereof may range from 0.01 to 10 wt. %, with a range of from 0.05 to 5% being particularly preferred.

The depilatory or external preparation according to the present invention is used as a drug, cosmetic or animal drug, and its use as an epilation-, depilation- or shaving-related cosmetic or drug is particularly preferred. Illustrative of such a cosmetic or drug are depilatories in the form of pastes, creams, aerosols and the like; depilatories in the form of waxes, jels, sheets and the like; after-treatments useful for the after-treatment of epilation or depilation, such as lotions and creams; antihidrotic and deodorant cosmetics such as deodorant lotions, deodorant powders, deodorant sprays and deodorant sticks; preshave treatments such as preshave lotions; shaving preparations such as shaving creams; and aftershave treatments such as aftershave lotions.

Further, the depilatory and external preparation according to the present invention may contain various ingredients generally used in drugs, cosmetics, quasi-drugs, animal drugs or the like, for example, purified water, ethanol, oiliness substances, humectants, thickeners, preservatives, emulsifiers, pharmaceutically active ingredients, powders, ultraviolet absorbers, colors, fragrances, and emulsion stabilizers.

EXAMPLES

Example 1

Depilation Inducing Effects of Endothelin

A solution of endothelin-1 (0.3 μg) in phosphate buffer solution (PBS), which contained 0.1% of bovine serum albumin (BSA), was intracutaneously administered (at 50 μL/site) to the dorsal part of a guinea pig. As a result, 10 days after the administration, hair shaft falling-off and formation of a marked depilation spot were observed at the site administered with endothelin-1, whereas no change was observed at a site administered with the solvent (0.1% BSA/PBS).

From the foregoing, it has been demonstrated that endothelin has depilation inducing effects.

Example 2

Growth-Phase Hair Follicle Inhibitory Effects of Endothelin

Solutions (1 μg, each) of endothelin-1, endothelin-2 and endotherin-3 in aliquots of phosphate buffer solution (PBS), which contained 0.1% of bovine serum albumin (BSA), were intracutaneously administered (at 50 μL/site) to the dorsal parts of guinea pigs, respectively, from which hair had been cut off by a hair clipper. Three days after the administration, hair was again cut off by a hair clipper from the administered sites. Two days after the cutting, the numbers of hair shafts grown per unit area at the administered sites were counted. As a result, a significant ($p<0.01$) decrease in the number of hair shafts was observed on the fifth day after the administration (FIG. 1).

From the foregoing, it has been demonstrated that the above-mentioned endothelin isoforms are effective for decreasing the number of growth-phase hair follicles.

Example 3

Figure 2:
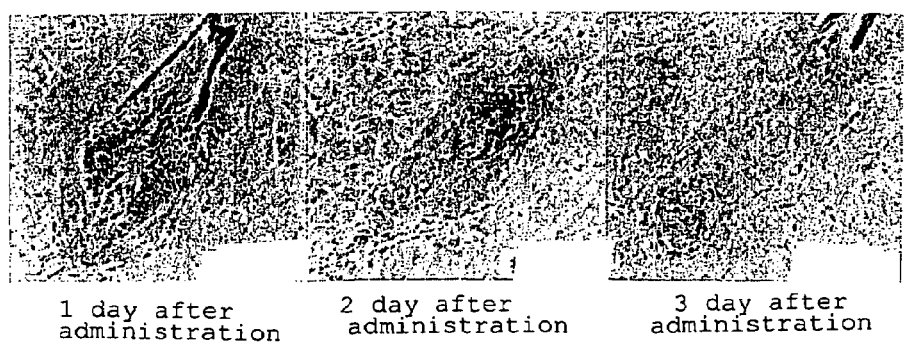
FIG. 2 micrographically shows structural changes of a hair follicle structure by the administration of endothelin.

Structural Changes of Hair Follicle Structure by the Administration of Endothelin A solution of endothelin-1 (0.3 μg) in phosphate buffer solution (PBS), which contained 1.1% of bovine serum albumin (BSA), was intracutaneously administered (at 50 μL/site) to the dorsal part of a guinea pig. After that, samples were collected day after day from the administered dorsal skin, and tissue samples were prepared by hematoxylin-eosin staining. As a result, a regressed image of a growth-phase hair follicle was observed on the $1^{st}$ day after the administration, and an image of a follicular tissue in transition phase was presented on the $3^{rd}$ day after the administration (FIG. 2).

From the foregoing, it is suggested that the growth-phase hair follicle inhibitory effects by the administration of endothelin are attributed to effects that cause transition of growth-phase hair follicles into resting-phase hair follicles (resting-phase hair follicle inducing effects).

Example 4

Effects of Concurrent Administration of Endothelin Inhibitor on the Endothelin-Induced Formation of Depilation Spot As described in Example 1, endothelin (0.3 μg) was intracutaneously administered to the dorsal part of each guinea pig, and PD142893 (10 μg) as an endothelin inhibitor was also administered concurrently.

The size of a depilation spot formed 10 days after the administration was determined in terms of a product of its long diameter and short diameter. The results are presented in Table 1. By the concurrent administration of PD142893, the formation of the depilation spot was significantly inhibited.

From those results, i.t is suggested that induction of a depilation spot by endothelin-1 is not a phenomenon caused by non-specific histotoxicity.

TABLE 1

Effects of administration of endothelin inhibitor on the
formation of endothelin-induced depilation spot

| Administered Ingredient | Product of long diameter and short diameter of depilation spot (mm$^2$) (mean ± S.D., N = 6) |
|---|---|
| Solvent (0.1% BSA/PBS) | 0.00 ± 0.00 |
| Endothelin-1 (0.3 μg) | 81.47 ± 6.53 |
| PD142893 (10 μg) | 0.00 ± 0.00 |
| Endothelin-1 + PD142893 | 41.30 ± 20.43 ($p < 0.01$ vs. endothelin-1 administration) |

Example 5

Growth Inhibitory Effects on Organ-Cultured Hair Follicles

Figure 3:
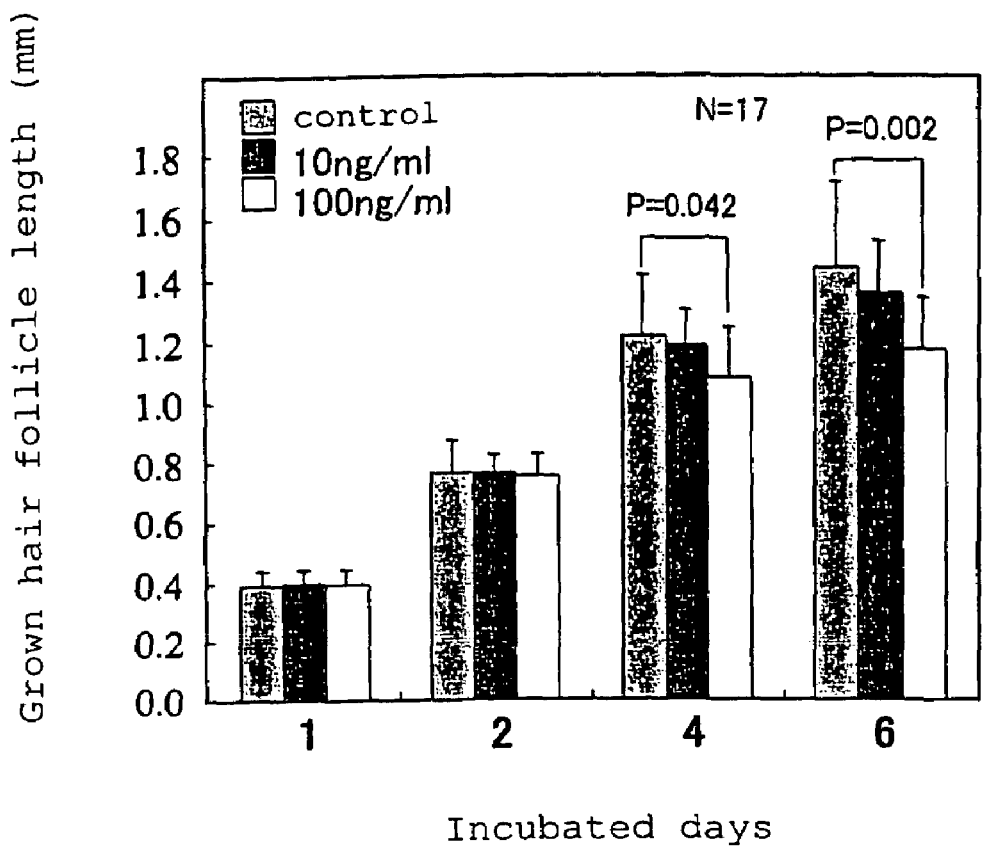
FIG. 3 is a histogram depicting growth inhibitory effects of endothelin against incubated hair follicles.
Figure 4:
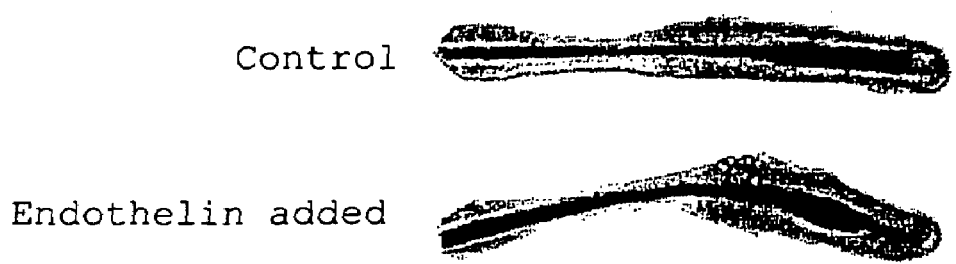
FIG. 4 micrographically depicts structural changes of incubated hair follicles by the addition of endothelin.

From a human scalp tissue, hair follicle organs in growth phase were surgically isolated under a stereomicroscope. Following a conventional procedure [Philpott M. P., et al., J. Cell Sci., 97, 463-471 (1990)], the isolated hair follicles were subjected to organ culture. Described specifically, endothelin-1 was added to William's E medium which contained L-glutamine (2 mM), hydrocortisone (10 ng/mL), insulin (10 μg/mL), sodium selenite (10 ng/mL) and transferrin (10 μg/mL). In the medium, the insolated hair follicles were incubated at 37° C. under a gaseous phase of 5% $CO_2$, during which grown hair follicle lengths were observed with days. As a result, significant hair growth inhibitory effects were observed on day 4 of incubation and the subsequent days in the group added with endothelin-1 compared with a control group in which endothelin-1 was not added (FIG. 3). Further, during that incubation period, a structural change of the endothelin-treated, growth-phase hair follicles into those similar to resting-phase hair follicles was observed (FIG. 4). Percent formations of regressed hair follicles with days are presented in Table 2.

From the results, it has become evident that addition of endothelin promotes transition of isolated human hair follicles from growth phase into regressing phase and inhibits their growth.

TABLE 2

Effects of endothelin on the percent
regression of growth-phase hair follicles

| Concentration of added endothelin (ng/mL) | Day 1 of incubation | Day 2 of incubation | Day 4 of incubation | Day 6 of incubation |
|---|---|---|---|---|
| 0 | 0.0 | 0.0 | 5.9 | 5.9 |
| 10 | 0.0 | 0.0 | 17.6 | 35.3 |
| 100 | 0.0 | 0.0 | 23.5 | 41.2 |

Example 6

Hair Growth Test in Mice

Endothelin-1 (0.5 mg) was dissolved in a mixed solution (2.5 mL) of polyethylene glycol 400 (average molecular weight: 400) and polyethylene glycol 3350 (average molecular weight: 3,350) (mixing ratio: 95/5) to prepare a hair growth inhibitor. Dorsal hair of each 8-week old C3H/HeN-Crj mouse was removed with a depilatory cream (over an area of 2×4 cm$^2$), and the hair growth inhibitor was applied to the depilated site once a day at a dose of 25 μL/application over 2 weeks. A group in which only the solvent was similarly applied was employed as a control group. To observe regrowth of hair, the above-described depilated site on day 14 after the depilation was photographed at a predetermined fixed magnification, and the percentage of a regrown hair area (regrown hair area/depilated area×100) was determined using an image analyzer. The results are presented in Table 3.

From the results, hair growth inhibitory effects by the application of endothelin to skin have become evident.

TABLE 3

Hair growth inhibitory effects by
the application of endothelin to skin

| Applied sample | Number of test animals | Percentage of regrown hair area on day 14 after depilation |
|---|---|---|
| Solvent | 6 | 10.98 |
| Endothelin-1 | 5 | 2.22 |

Example 7

Formulation Examples (1) Hair Growth Inhibitory Lotion

TABLE 4

| | Ingredient | (wt. %) |
|---|---|---|
| A | Polyoxyethylene-hydrogenated castor oil | 0.8 |
| | Ethanol | 30.0 |
| B | Endothelin-1 | 0.5 |
| | Sodium dodecylsulfate | 0.12 |
| | Dodecylmethylamine oxide | 0.18 |
| | Isopyl alcohol | 15.0 |
| | Benzyl alcohol | 15.0 |
| | Glycerin | 2.0 |
| | Purified water | Balance |

The ingredients belonging to Group A were dissolved. On the side, the ingredients belonging to Group B were dissolved. Solution B was added to Solution A, followed by stirring into a uniform mixture to obtain a hair growth inhibitory lotion.

(2) Hair Growth Inhibitory Cream

TABLE 5

| | Ingredient | (wt. %) |
|---|---|---|
| A | Liquid paraffin | 10.0 |
| | Squalane | 7.0 |
| | Jojoba oil | 3.0 |
| | Solid paraffin | 3.0 |
| | Polyoxyethylene cetyl ether | 2.0 |
| | Sorbitan sesquioleate | 1.0 |
| | Potassium hydroxide | 0.1 |
| B | Endothelin-1 | 0.5 |
| | Glycerin | 3.0 |
| | Ethylparaben | 0.1 |
| | Purified water | Balance |

The ingredients belonging to Group A were dissolved. On the side, the ingredients belonging to Group B were dissolved under heat. Solution B was added to Solution A, followed by stirring into a uniform mixture. Subsequent to emulsification, the resultant emulsion was cooled to obtain a hair growth inhibitory cream.

(3) Hair Growth Inhibitory Foam

TABLE 6

| | Ingredient | (wt. %) |
|---|---|---|
| A | ILA1620 | 1.0 |
| | Cetanol | 0.1 |
| | Propylene glycol | 2.0 |
| | Dimethyl corn oil | 2.0 |
| | Polyoxyethylene-hydrogenated castor oil | 2.5 |
| | Liquid paraffin | 1.0 |
| | Polyvinyl pyrrolidone | 0.5 |
| | Methylparaben | 0.2 |
| | Ethanol | 10.0 |
| | Purified water | Balance |
| B | Liquefied petroleum gas (propellant) | 4.0 |

The ingredients belonging to Group A were combined into a uniform mixture and then placed in a can. By a method known per se in the art, the ingredient B was filled in the can to produce a hair growth inhibitory foam.

(4) Aerosol

TABLE 7

| | Ingredient | (wt. %) |
|---|---|---|
| A | BQ3020 | 0.05 |
| | Cetanol | 1.2 |
| | Propylene glycol | 4.0 |
| | Ethanol | 8.0 |
| | Purified water | Balance |
| B | Liquefied petroleum gas (propellant) | 4.0 |

The ingredients belonging to Group A were combined into a uniform mixture and then placed in a can. By a method known per se in the art, the ingredient B was filled in the can to produce an aerosol.

INDUSTRIAL APPLICABILITY

The depilatories and external preparations according to the present invention inhibit the growth of hair in mammalian skin. Their application as drugs or cosmetics to the human body, therefore, permits safe and efficient removal of hair from the body. Further, their use, for example, as wool harvesting preparations for the harvest of wool makes it possible to harvest wool of high quality.

The invention claimed is:

1. A method of depilation, comprising:
transdermally administering or topically intracutaneously applying a depilatory-containing composition containing an active ingredient selected from the group consisting of endothelin and an endothelin agonist to a subject to achieve the removal of hair from said subject, wherein the depilatory-containing composition contains at least one additive selected from the group consisting of a keratolytic agent, a salt of a keratolytic agent, thioglycolic acid, a salt of thioglycolic acid, purified water, ethanol, an oiliness substance, a humectant, a thickener, a preservative, an emulsifier, an ultraviolet absorber, a color, a fragrance, and an emulsion stabilizer.

2. The method according to claim 1, wherein said subject is a human being or a cow.

3. The method according to claim 2, wherein said subject is a cow.

4. The method according to claim 1, wherein said depilatory-containing composition is transdermally administered to said subject.

5. The method according to claim 1, wherein said depilatory-containing composition is topically intracutaneously administered to the skin of said subject.

6. The method according to claim 1, wherein said active ingredient is in a concentration in the range of from 0.01 to 10 wt. % based on the weight of the composition.

7. The method according to claim 1, wherein the amount of said active ingredient administered to said subject ranges from 0.1 to 100 µg/administration.

8. The method according to claim 1, wherein said depilatory-containing composition is in the form of a paste, a cream, an aerosol, a wax, a gel, a sheet, a lotion, a cream, a deodorant powder, a deodorant spray, a deodorant stick, a preshave lotion, a shaving cream or an aftershave lotion.

* * * * *